United States Patent [19]

Iacoviello

[11] 4,449,978
[45] May 22, 1984

[54] NONWOVEN PRODUCTS HAVING LOW RESIDUAL FREE FORMALDEHYDE CONTENT

[75] Inventor: John G. Iacoviello, Allentown, Pa.

[73] Assignee: Air Products and Chemicals, Inc., Allentown, Pa.

[21] Appl. No.: 481,216

[22] Filed: Apr. 1, 1983

Related U.S. Application Data

[63] Continuation-in-part of Ser. No. 297,583, Aug. 31, 1981, abandoned.

[51] Int. Cl.³ .................. A61F 13/16; B05D 3/02; B32B 23/16; D04H 1/64
[52] U.S. Cl. .................. 604/372; 427/389.9; 428/290
[58] Field of Search ............... 428/290; 427/389.9; 604/372

[56] References Cited

U.S. PATENT DOCUMENTS

3,081,197 3/1963 Adelman .
3,137,589 6/1964 Reinhard et al. .
3,380,851 4/1968 Lindemann et al. .
3,732,184 5/1973 Lindemann et al. .
3,922,462 11/1975 Katz et al. .

OTHER PUBLICATIONS

Pierce et al., *Textile Res. J.*, (1973) pp. 294–299.
Hebeish, *Textile Res. J.*, (1976) pp. 465–466.
*Chemical Abstracts* 68: 70145; 69: 20384; 76: 47347.

*Primary Examiner*—James C. Cannon
*Attorney, Agent, or Firm*—Michael Leach; J. C. Simmons; E. E. Innis

[57] ABSTRACT

A nonwoven product formed from a nonwoven web of fibers bonded together with a binder comprising an interpolymer of vinyl acetate/ethylene/N-methylol acrylamide/acrylamide, the interpolymer comprising about 5 to 40 wt % ethylene and an amount of N-methylol acrylamide and acrylamide which is about 3.0 to 10 wt % of the interpolymer, the N-methylol acrylamide being about 1.75 to 3.5 wt % and the acrylamide about 1.25 to 8.25 wt %. Such nonwoven products have a low residual free formaldehyde content and good tensile properties.

46 Claims, No Drawings

NONWOVEN PRODUCTS HAVING LOW RESIDUAL FREE FORMALDEHYDE CONTENT

CROSS REFERENCE TO RELATED APPLICATION

This application is a continuation-in-part of pending Application Ser. No. 06/297,583 filed Aug. 31, 1981, and now abandoned, which is incorporated by reference.

TECHNICAL FIELD

This invention relates to binder compositions which are used to bind together a loosely assembled mass of fibers into a nonwoven product. More particularly, this invention relates to nonwoven products bonded with a binder composition comprising an interpolymer containing N-methylol acrylamide units and having low free formaldehyde content.

BACKGROUND OF THE INVENTION

Nonwoven products of fabrics, comprise loosely assembled webs or masses of fibers bound together with an adhesive binder. Adequately bonded nonwoven fabrics have advantages over woven fabrics for a large variety of uses. It is known to form bonded nonwoven fabrics by impregnating, printing or otherwise depositing an adhesive bonding composition on a base web predominantly comprising relatively long fibers, including those of textile length of from about ½ inch (1.27 cm) to about 2½ inch (6.35 cm), or more. These fibers may be of cellulosic or polymeric materials such as polyesters, polyamides, polyacrylates and the like. The base web of nonwoven fibers, to which the binder is applied, can be produced by carding, garnetting, airlaying, papermaking procedures, or other known operations. The operation of bonding fibers in place is much less expensive than conventional spinning and weaving. In comparison with woven fabric, the bonded nonwoven fabrics can be made in a much greater range of thicknesses per unit weight, with more homogeneous structures, no unravelling tendency, and with greater water absorbancy, porosity and resiliency, when required.

Representative of various binder compositions used in the art are U.S. Pat. Nos. 3,081,197; 3,137,589; and 3,380,851.

U.S. Pat. No. 3,081,197 discloses a nonwoven binder comprising interpolymers of vinyl acetate, another polymerizable compound as an internal plasticizer, and a post-curable comonomer such as N-methylol acrylamide.

U.S. Pat. No. 3,137,589 discloses binders comprising a copolymer of an alpha,beta-unsaturated carboxylic acid amide substituted on the nitrogen by at least one methylol group and another unsaturated polymerizable compound.

U.S. Pat. No. 3,380,851 discloses a binder comprising an interpolymer of vinyl acetate-ethylene-N-methylol acrylamide.

Such N-methylol acrylamide-type containing binder compositions are typically prepared by reacting a formaldehyde releasing material with a polymer containing acrylic acid amide units or by polymerizing the N-methylol acrylamide monomer with other ethylenically unsaturated monomers, the N-methylol acrylamide monomer having been formed by the reaction of a formaldehyde releasing material with acrylamide. In the manufacture of nonwoven binders, N-methylol acrylamide is typically used at a level of about 3–5%, based on total solids. These binder compositions afford objectionable quantities of free formaldehyde in nonwoven products such as disposable baby diapers. By "free formaldehyde" I mean that formaldehyde which is extractable with water, whether or not as a consequence of the following equilibrium reaction I which, for illustration, depicts a polymerized N-methylol acrylamide unit.

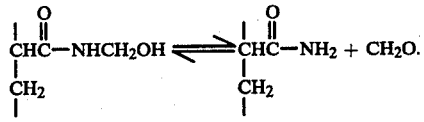

The chemical industry and, particularly, the disposable nonwovens market segment has become aware of the potential hazards of formaldehyde. Accordingly, the use of formaldehyde containing and formaldehyde releasing polymers has come under scrutiny.

There is a need for an N-methylol acrylamide containing binder for making nonwoven products containing low levels of free formaldehyde while maintaining acceptable wet and dry tensile properties.

SUMMARY OF THE INVENTION

The above need has been satisfied by my invention of an N-methylol acrylamide containing binder composition for a nonwoven product formed from a nonwoven web of fibers. The web of fibers are bonded together with a binder comprising an interpolymer of vinyl acetate/ethylene/an N-methylol acrylamide/an acrylamide. The interpolymer contains about 5 to 40 wt % ethylene and a total of an N-methylol acrylamide and an acrylamide which is about 3 to 10 wt % of the interpolymer with the N-methylol acrylamide at about 1.75 to 3.5 wt % and the acrylamide at about 1.25 to 8.25 wt %. The nonwoven product contains an amount of the interpolymer binder which is at least sufficient to bind the fibers together to form a self-sustaining web.

As an advantage of the invention, nonwoven products bonded with such binder composition comprising an interpolymer of vinyl acetate/ethylene/an N-methylol acrylamide/an acrylamide have a low residual free formaldehyde content after drying and curing while maintaining good nonwoven tensile properties.

Another advantage is the ability to use N-methylol acrylamide/acrylamide containing emulsion binder compositions which have a relatively high level of free formaldehyde to produce nonwoven products having low residual free formaldehyde content.

DETAILED DESCRIPTION OF THE INVENTION

Commercially available N-methylol acrylamide which is used in the preparation of nonwoven binder emulsion compositions is typically a 48% aqueous solution and contains free formaldehyde at a level up to about 2%. When such N-methylol acrylamide containing emulsion compositions are applied to a mass of nonwoven fibers, the cured nonwoven product may contain free formaldehyde on the order of 50 to 60 ppm or more.

The source of residual free formaldehyde in the cured, bonded nonwoven product is believed to be the N-methylol acrylamide component of the interpolymer in the binder composition. During the curing step of a nonwoven product which has been saturated with a N-methylol acrylamide containing binder composition, two methylol groups of the N-methylol acrylamide units react to liberate water forming ether cross-linkages according the following reaction scheme II:

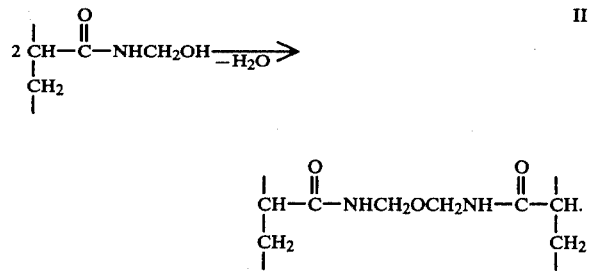

Any unreacted, non-cross-linked N-methylol acrylamide units after the curing step would be the source of free formaldehyde as a result of the equilibrium reaction I.

I have discovered that the use of acrylamide to replace some of the N-methylol acrylamide in typical binder compositions comprising an interpolymer containing vinyl acetate/ethylene/N-methylol acrylamide affords a new binder composition which, when applied to a loosely assembled web of fibers, yields a nonwoven product with low free formaldehyde. More specifically, the nonwoven product is bonded together with a binder comprising an interpolymer of vinyl acetate/ethylene/N-methylol acrylamide/acrylamide which contains about 5 to 40 wt % ethylene and an amount of N-methylol acrylamide and acrylamide which is about 3 to 10 wt % of the interpolymer with the N-methylol acrylamide at about 1.75 to 3.5 wt % and the acrylamide at about 1.25 to 8.25 wt %.

The nonwoven product is characterized by a low free formaldehyde content after drying and curing at a binder add-on which is sufficient to bind the fiber web together. In general, a sufficient amount of binder add-on may be at least about 3 wt% on a dry basis, preferably at 10 to 100 wt% binder add-on, on a dry basis. Typically, the dried and cured nonwoven product will have a free formaldehyde content of less than 50 ppm and preferably, in many cases, below about 25 or even 15 ppm. Such levels are feasible at about 50 wt% binder add-on, on a dry basis. Levels of free formaldehyde of about 10 ppm or less are considered almost formaldehyde-free and are attainable by this invention. For example, in paper nonwovens at about 20 wt% or less binder add-on, the free formaldehyde level is often less than 10 ppm. X wt% binder add-on, on a dry basis, means X grams polymer binder per 100 grams nonwoven fibers.

The mechanism by which the N-methylol acrylamide and acrylamide units in the interpolymer interact during the curing process to afford a nonwoven product having a low level of free formaldehyde is not clearly understood. It may be reasoned that by replacing some of the N-methylol acrylamide units with acrylamide units there will be less methylol groups capable of generating free formaldehyde via the equilibrium reaction.

Surprisingly, however, the level of free formaldehyde in the cured nonwoven fabric of this invention is lower than would be expected by simply replacing a particular percentage of the N-methylol acrylamide monomer with acrylamide monomer. For example, when 50% of N-methylol acrylamide is replaced with an amount of acrylamide in a particular binder composition, the resulting binder composition affords a nonwoven product having a free formaldehyde content which is much less than the expected 50% reduction in residual free formaldehyde. In addition, it appears to be irrelevant to the residual free formaldehyde content of the nonwoven product whether the binder emulsion composition is prepared from a N-methylol acrylamide-acrylamide solution which contains about 1% free formaldehyde or from a monomer solution which contains only about 0.1 to 0.2% free formaldehyde. As demonstrated in the Examples, both such binder emulsion compositions yield nonwovens having low levels of free formaldehyde even though one binder emulsion has a much higher free formaldehyde content relative to the other.

Contemplated as functional equivalents of the N-methylol acrylamide and acrylamide monomers used in the practice of this invention are N-methylol methacrylamide and methacrylamide, respectively.

Preferably, the acrylamide monomers are present in a N-methylol acrylamide:acrylamide molar ratio which is about 1:1; i.e. about equimolar.

It is also preferred that the combined N-methylol acrylamide and acrylamide monomers amount to about 4 to 5 wt % of the interpolymer. The minimum amount of N-methylol acrylamide in the binder composition which is necessary to provide upon curing a nonwoven product having acceptable wet and dry tensile properties is about 1.75 wt % based on interpolymer. The maximum amount of N-methylol acrylamide, which in combination with acrylamide yields a nonwoven product having acceptable amounts of free formaldehyde, is about 3.5 wt % of the interpolymer.

A minimum amount of acrylamide at 1.25 wt % is needed for good cross-linking, emulsion stability and acceptable levels of free formaldehyde.

While U.S. Pat. No. 3,732,184 discloses a specific example for preparing an aqueous polymer emulsion from a monomer mixture comprising butyl acrylate, acrylonitrile, itaconic acid, N-methylol acrylamide and acrylamide, there is no teaching with respect to nonwoven fabrics containing low free formaldehyde.

Suitable as the binder composition is a vinyl acetate/ethylene/N-methylol acrylamide/acrylamide interpolymer latex which is prepared by the following process.

Vinyl acetate and ethylene are copolymerized in the presence of the N-methylol acrylamide and acrylamide monomer mixture in an aqueous medium under pressures not exceeding 100 atmospheres in the presence of a catalyst and at least one emulsifying agent, the aqueous system being maintained by a suitable buffering agent at a pH of 2 to 6, the catalyst being added incrementally. The process is a batch process which involves first a homogenization in which the vinyl acetate suspended in water is thoroughly agitated in the presence of ethylene under the working pressure to effect solution of the ethylene in the vinyl acetate while the reaction medium is gradually heated to polymerization temperature. The homogenization period is followed by a polymerization period during which the catalyst, which consists of a main catalyst, or initiator, and may include an activator, is added incrementally. The N-methylol acrylamide and the acrylamide are similarly added incrementally, the pressure in the system being maintained substantially constant by application of a constant ethylene pressure.

Various free-radical forming catalysts can be used in carrying out the polymerization of the monomers, such as peroxide compounds. Combination type catalysts employing both reducing agents and oxidizing agents can also be used. The use of this type of combined catalyst is generally referred to in the art as "redox polymerization" or "redox system." The reducing agent is also often referred to as an activator and the oxidizing agent as an initiator. Suitable reducing agents or activators include bisulfites, sulfoxylates, or other compounds having reducing properties such as ferrous salts, and tertiary aromatic amines, e.g. N,N-dimethylaniline. The oxidizing agents or initiators include hydrogen peroxide, organic peroxides such as benzoyl peroxide, t-butyl hydroperoxide and the like, persulfates, such as ammonium or potassium persulfate, perborates, and the like. Specific combination type catalysts or redox systems which can be used include hydrogen peroxide and zinc formaldehyde sulfoxylate; hydrogen peroxide, ammonium persulfate, or potassium persulfate, with sodium metabisulfite, sodium bisulfite, ferrous sulfate, dimethylaniline, zinc formaldehyde sulfoxylate or sodium formaldehyde sulfoxylate. Other types of catalysts that are well known in the art can also be used to polymerize the monomers.

The catalyst is employed in an amount of 0.1 to 2%, preferably 0.25 to 0.75% based on the weight of vinyl acetate introduced into the system. The activator is ordinarily added in aqueous solution and the amount of activator is generally 0.25 to 1 times the amount of catalyst.

The emulsifying agents which are suitably used are nonionic. Suitable nonionic emulsifying agents include polyoxyethylene condensates. Polyoxyethylene condensates may be represented by the general formula:

$$R-CH_2CH_2O-_nH$$

where R is the residue of a fatty alcohol containing 10 to 18 carbon atoms, an alkylphenol, a fatty acid containing 10 to 18 carbon atoms, an amide, an amine, or a mercaptan, and where n is an integer of 1 or above.

A single emulsifying agent can be used, or the emulsifying agents can be used in combination. When combinations of emulsifying agents are used, it is advantageous to use a relatively hydrophobic emulsifying agent in combination with a relatively hydrophilic agent. A relatively hydrophobic agent is one having a cloud point in 1% aqueous solution below 190° F. (88° C.) and a relatively hydrophilic agent is one having a cloud point in 1% aqueous solution of 190° F. (88° C.) or above.

The concentration range of the total amount of emulsifying agents useful is from 0.5 to 5% based on the aqueous phase of the latex regardless of the solids content.

Latex stabilizers are also advantageously used. When the vinyl acetate-ethylene copolymer latexes are to have a small average particle size, for example, below 0.25 microns, an ethylenically unsaturated acid having up to 6 carbon atoms is used as the stabilizer, such as acrylic acid, maleic acid, and the like. These unsaturated acids impart increased stability to the latexes. They tend to copolymerize with the monomers in the system. The amount of unsaturated acid used is suitably 0.1 to 3 wt % based on interpolymer, preferably 0.2 to 1 wt %.

On the other hand, when the latex has an average particle size above 0.25 microns, a protective colloid can be used in the polymerization mixture as the stabilizing agent. It is advantageous to maintain the colloid content of the latexes between about 0.05 and 2 wt % based on the total latex. Polyvinyl alcohol and hydroxyethyl cellulose are examples of particularly advantageous colloids.

If it is desired to maintain the pH of the system at a desired value, there may suitably be added an alkaline buffering agent of any convenient type which is compatible with the stabilizing agent. The amount of buffer is generally about 0.1 to 0.5 wt % based on the monomers.

For more details concerning redox systems, emulsifying agents, latex stabilizers, protective colloids, and buffers, see U.S. Pat. No. 3,380,851, the disclosure of which is hereby incorporated by reference. This patent is directed vinyl acetate/ethylene/N-methylol acrylamide latexes.

Latexes of relatively high solids contents can be directly produced and thus the products generally have solids contents of 45 to 60%. They can, of course, be easily thinned by the addition of water to lower solids contents of any desired value.

The reaction temperature can be controlled by the rate of catalyst addition and by the rate of the heat dissipation. Generally we have found that it is advantageous to maintain a mean temperature of about 50° C. during the polymerization of the monomers and to avoid temperatures much in excess of 80° C. While temperatures as low as 0° C. can be used, economically the lower temperature limit is about 30° C.

The reaction time will also vary depending upon other variables such as the temperature, the catalyst, and the desired extent of the polymerization. It is generally desirable to continue the reaction until less than 0.5% of the vinyl acetate remains unreacted.

In carrying out the polymerization, an amount of the vinyl acetate is initially charged to the polymerization vessel and saturated with ethylene. Most advantageously, at least about 10% of the total vinyl acetate to be polymerized is initially charged, preferably at least about 20%, and the remainder of the vinyl acetate is incrementally added during the course of the polymerization. The charging of all of the vinyl acetate initially is also contemplated with no additional incremental supply. When reference is made to incremental addition, whether of vinyl acetate, N-methylol acrylamide, acrylamide, catalysts, or activator, substantially uniform additions, both with respect to quantity and time, are contemplated. Such additions are also referred to as "delay" additions.

The quantity of ethylene entering into the copolymer is influenced by the pressure, the agitation, and the viscosity of the polymerization medium. Thus, to increase the ethylene content of the copolymer higher pressures, greater agitation and a low viscosity are employed.

The process of forming the vinyl acetate/ethylene/N-methylol acrylamide/acrylamide interpolymer latexes generally comprises the preparation of an aqueous solution containing at least some of emulsifying agent and stabilizer, and the pH buffering system. This aqueous solution and the initial charge of vinyl acetate are added to the polymerization vessel and ethylene pressure is applied to the desired value. As previously mentioned, the mixture is thoroughly agitated to dissolve ethylene in the vinyl acetate and in the water phase. Conveniently, the charge is brought to polymerization temperature during this agitation period. Agitation can be effected by shaking, by means of an agitator, or other known mechanism. The polymerization is then initiated by introducing initial amounts of the catalyst and of the activator when used. After polymerization has started, the catalyst and the activator are incrementally added as required to continue polymerization, and the N-methylol acrylamide and acrylamide monomer mix, and the remaining vinyl acetate if any, is similarly added. The N-methylol acrylamide and acrylamide monomers may be added as separate delays.

As mentioned, the reaction is generally continued until the residual vinyl acetate content is below 0.5%. The completed reaction product is then allowed to cool to about room temperature while sealed from the atmosphere. The pH is then suitably adjusted to a value in the range of 4.5 to 7, preferably 6 to 6.5 to insure maximum stability.

Another method for producing vinyl acetate-ethylene containing copolymers which is preferred for preparing vinyl acetate/ethylene/N-methylol acrylamide/acrylamide interpolymer emulsions of this invention comprises first forming an aqueous emulsion of vinyl acetate and stabilizer and charging this emulsion to a reactor. The reactor is pressurized with ethylene to an ethylene-equilibrium pressure of about 200 to 500 psig. The resulting reaction mixture is adjusted to a temperature from about 10° to 30° C. Polymerization is initiated by the addition of a catalyst at a rate such that the reaction mixture is brought to a temperature of from 45° to 85° C., preferably 50° to 60° C., within a period of one hour or less, preferably 30 minutes. The polymerization is continued until the vinyl acetate content is reduced below about 0.7 wt % of the copolymers.

The N-methylol acrylamide and acrylamide monomers can be added to the reaction vessel with the initial charge or as a delay or a combination of the two.

This latter polymerization process is the subject of U.S. Pat. No. 4,332,850 which is incorporated by reference.

The vinyl acetate/ethylene/N-methylol acrylamide/acrylamide binder is used to prepare nonwoven products, or fabrics, by a variety of methods known to the art which, in general, involve the impregnation of a loosely assembled mass of fibers with the binder latex, followed by moderate heating to dry the mass. In the case of the present invention, this moderate heating also serves to cure the binder by forming a cross-linked interpolymer. Before the binder is applied it is, of course, mixed with a suitable catalyst of the N-methylol acrylamide. Thus, acid catalysts such as mineral acids, e.g. hydrogen chloride, or organic acids, e.g. oxalic acid, or acid salts such as ammonium chloride, are suitably used as known in the art. The amount of catalyst is generally about 0.5 to 2% of the total resin.

The starting layer or mass can be formed by any one of the conventional techniques for depositing or arranging fibers in a web or layer. These techniques include carding, garnetting, air-laying, and the like. Individual webs or thin layers formed by one or more of these techniques can also be laminated to provide a thicker layer for conversion into a fabric. Typically, the fibers extend in a plurality of diverse directions in general alignment with the major plane of the fabric, overlapping, intersecting and supporting one another to form an open, porous structure. When reference is made to "cellulose" fibers, those fibers containing predominently $C_6H_{10}O_5$ groupings are meant. Thus, examples of the fibers to be used in the starting layer are the natural cellulose fibers such as wood pulp, cotton and hemp and the synthetic cellulose fibers such as rayon, and regenerated cellulose. Often the fibrous starting layer contains at least 50% cellulose fibers, whether they be natural or synthetic, or a combination thereof. Often the fibers in the starting layer may comprise natural fibers such as wool, or jute; artificial fibers such as cellulose acetate; synthetic fibers such as polyamides, nylon, polyesters, acrylics, polyolefins, i.e. polyethylene, polyvinyl chloride, polyurethane, and the like, alone or in combination with one another.

The fibrous starting layer is subjected to at least one of the several types of bonding operations to anchor the individual fibers together to form a self-sustaining web. Some of the better known methods of bonding are overall impregnation, or printing the web with intermittent or continuous straight or wavy lines or areas of binder extending generally transversely or diagonally across the web and additionally, if desired, along the web.

The amount of binder, calculated on a dry basis, applied to the fibrous starting web should be at least about 3 wt% and suitably ranges from about 10 to about 100% or more by weight of the starting web, preferably from about 10 to about 50% by weight of the starting web. The impregnated web is then dried and cured. Thus the fabrics are suitably dried by passing them through an air oven or the like and then through a curing oven. Typical conditions to achieve optimal cross-linking are sufficient time and temperature such as drying at 150° to 200° F. (66° to 93° C.) for 4 to 6 minutes, followed by curing at 300° to 310° F. (149° to 154° C.) for 3 to 5 minutes or more. However, other time-temperature relationships can be employed as is well known in the art, shorter times at higher temperatures or longer times at lower temperatures being used.

Nonwoven fabrics, or products, prepared in accordance with this invention have wet and dry tensile strength values comparable to those nonwoven fabrics prepared using prior art vinyl acetate-ethylene-N-methylol acrylamide binders. More importantly, these nonwoven fabrics have the outstanding advantage of low residual free formaldehyde.

External plasticizers are not needed with the binders of this invention, however, they can be used to modify the properties of the fabrics when desired. Thus some external plasticizers can be added when an extremely soft fabric is desired. It has been observed that the flexibility of the fabric can be increased by the addition of a hydrophobic external plasticizer to the binder composition without loss of desirable properties. Examples of external plasticizers which are suitably used include dibutoxyethylphthalate, dibutyl phthalate, tricresyl phosphate, and low molecular weight polyesters.

Illustrative of the types of nonwoven products which can be made from wood pulp and, optionally, other fibers utilizing the invention are paper nonwovens such as disposable diapers, consumer towels, disposable wipes and filtration products.

The following examples are provided to illustrate the invention and are not intended to restrict the scope thereof:

EXAMPLE 1

The polymerization of various vinyl acetate-ethylene/N-methylol acrylamide/acrylamide systems (Runs 1-15) was carried out in a 15 gallon stirred, stainless steel reaction vessel equipped with a jacket, the agitation system involving 2 turbine blades.

In preparing the binder latex of Run 1 the following initial charge was introduced into the reaction vessel.

| INITIAL CHARGE | |
|---|---|
| Vinyl acetate | 22700 g |
| Alipal CO—433 (30%) | 1966 g |
| Igepal CO—430 | 250 g |
| FeSO$_4$ | 1 g |
| H$_2$O | 13620 g |

Alipal CO-433 and Igepal CO-430 are trademarks for ethoxylated alkyl phenol emulsifying agents sold by GAF Corporation, Chemical Products.

No adjustment was made to the pH of the aqueous initial charge which was at a temperature of about 25° C. Ethylene was introduced below the surface of the liquid in the reaction vessel until the desired initial pressure of 460 psig was achieved in order that the interpolymer would have a vinyl acetate:ethylene ratio of about 80:20. Approximately 15 minutes agitation was effected to permit the ethylene to become dissolved and equilibrated in the vinyl acetate. Upon equilibration 11.36 grams of zinc formaldehyde sulfoxylate in a 7.1% aqueous solution was added prior to initiation.

The following three aqueous solutions were intermittently added to the reaction vessel over the course of the reaction, i.e. on a delay basis.

| DELAY CHARGES | |
|---|---|
| 20% N—methylol acrylamide + acrylamide | 5963 g |
| 2% Hydrogen peroxide | 715 g |
| 7.1% Zinc formaldehyde sulfoxylate | 718 g |

The catalyst comprising the 2% aqueous solution of hydrogen peroxide was added to the reaction vessel to initiate the polymerization reaction at such a rate that the reaction vessel contents was brought to a reaction temperature of about 50° C. within about 60 minutes. Also, upon initiation of the polymerization reaction the delay monomer solution comprising N-methylol acrylamide and acrylamide was added over a period of about 2.5 hours. The zinc formaldehyde sulfoxylate delay solution was added during the run. After the reaction vessel contents had been maintained at about 50° C. for about 3 hours and 14.3 grams hydrogen peroxide and 50.3 grams of zinc formaldehyde sulfoxylate had been added as their respective solutions, the reaction was terminated by cooling.

Table I presents the various amounts of N-methylol acrylamide (NMA) and acrylamide (AM) composing the 20% monomer delay solution in each of Runs 1 through 15. The vinyl acetate, ethylene, surfactants, and ferrous sulfate contents in the initial charge for Runs 2 to 15 were identical to that of Run 1. The delay additions of 2% hydrogen peroxide and 7.1% zinc formaldehyde sulfoxylate were comparable. The amount of water in the initial charge varied from about 13,000 to 15,000 grams for Runs 2 to 15.

In Runs 9 through 15, 15 grams of sodium acetate in about 85 grams of water, 11.36 grams of zinc formaldehyde sulfoxylate as a 7.1% aqueous solution and sufficient amount of concentrated acetic acid to adjust the pH to about 4.4 were added to the initial charge.

In Runs 4, 6, 7 and 8 a portion of the acrylamide monomer or the N-methylol acrylamide monomer was present in the initial charge. The aqueous mixtures of N-methylol acrylamide and acylamide used in Runs 1, 14 and 15 were specially prepared by American Cyanamide Corporation as a 50 wt % solution and had a free formaldehyde concentration of about 0.1 to 0.2 wt %. The remaining mixtures of N-methylol acrylamide and acrylamide used in Runs 2 through 13 were prepared by mixing an aqueous acrylamide solution with a commercial 48% aqueous N-methylol acrylamide solution having a free formaldehyde content of about 2 wt %. Accordingly, the resulting binder latexes had free formaldehyde contents (PPM) as indicated in Table I.

The latexes of Runs 1, 14 and 15 which were produced from the specially prepared, low (0.1 to 0.2%) free formaldehyde monomer mixture of N-methylol acrylamide and acrylamide had significantly lower free formaldehyde concentrations ranging from about 125 to 200 ppm than the latexes prepared from the mixture of acrylamide and the 48% aqueous N-methylol acrylamide solution having 2 wt% free formaldehyde. These latter latexes had free formaldehyde levels ranging from about 250 to 570 ppm. The latexes of Runs 8-11 which did not contain acrylamide in addition to the N-methylol acrylamide had free formaldehyde levels ranging from about 540 to 800 ppm.

TABLE I

| RUN | MONOMER DELAY NMA % based on interpolymer | MONOMER DELAY AM % based on interpolymer | MOLE RATIO NMA/AM | Tg [°C.] | FREE CH$_2$O PPM | REMARKS |
|---|---|---|---|---|---|---|
| 1 | *2.4 | 1.99 | .84:1 | 1.5 | 188 | |
| 2 | 1.75 | 1.23 | 1.0:1 | 3.5 | — | |
| 3 | 2.5 | 2.5 | .70:1 | 3 | 405 | |
| 4 | 1.75 | 2.0 | .62:1 | 1 | 329 | 22% AM in initial charge |
| 5 | 2.0 | 2.0 | .70:1 | 5 | 404 | |
| 6 | 3.5 | 3.0 | .82:1 | 2.5 | 567 | 25% AM in initial charge |
| 7 | 1.75 | 1.5 | .82:1 | 5.5 | 377 | 20% AM in initial charge |
| 8 | 3.5 | — | — | 5.5 | 732 | 10% NMA in initial charge |
| 9 | 5 | — | — | 2.5 | 541 | |
| 10 | 5 | — | — | 2 | 790 | |
| 11 | 3.5 | — | — | 3 | — | |
| 12 | 2.5 | 2.0 | .88:1 | 2 | 352 | |
| 13 | 1.75 | 1.23 | 1.0:1 | 3 | 258 | |
| 14 | *2.6 | 1.9 | .96:1 | 2 | 138 | |
| 15 | *2.6 | 1.9 | .96:1 | 2 | 128 | |

*Aqueous mixture of NMA and AM contained about 0.1 to 0.2 wt % free formaldehyde.

EXAMPLE II

The binder emulsions of Runs 1 to 8 were analyzed for paper web formaldehyde contribution. A typical prior art vinyl acetate/ethylene/N-methylol acrylamide binder composition containing 5 wt% N-methylol acrylamide based on interpolymer was prepared according to Run 1 for comparative purposes as a standard binder emulsion (STD). Whatman No. 4 chromatography paper was padded at 10 and 20% add-on levels with the aqueous emulsion containing 1% ammonium chloride as the curing catalyst. The padded paper was heated 5 minutes at 300° F. (149° C.).

The procedure for testing for free formaldehyde is a colorimetric method intended for the determination of free formaldehyde in nonwoven fabrics.

The formaldehyde is extracted with deionized water. The colorimetric analysis is based on the reaction of formaldehyde with acetylacetone in an ammonium acetate buffer. The absorbents of the yellow-colored product is measured on a visible spectrophotometer at 412 nm and the concentration of free formaldehyde is determined with reference to a standard calibration curve.

Acetylacetone Solution

Dissolve 150±0.1 g ammonium acetate in deionized water and quantitatively transfer the solution to a 100 ml volumetric flask. Pipet 3.0 ml glacial acetic acid and 2.0 ml acetylacetone into the flask. Dilute to volume with deionized water. Mix well and protect from light.

Standard Solutions

Solution A—Weigh to the nearest 0.1 mg, 10 g formaldehyde solution (37%) into a 100 ml volumetric flask. Dilute to volume with deionized water and mix well.

Solution B—Pipet 10.0 ml Solution A into a 1,000 ml volumetric flask. Dilute to volume with deionized water and mix well.

Solution C—Pipet 10.0 ml Solution B into a 1,000 ml volumetric flask. Dilute to volume with deionized water and mix well. The concentration of Standard Solution C (about 4 ug/ml) is calculated as follows:

$$\text{Weight HCHO solution (g)} \times \frac{\% \text{ assay}}{100} = \mu g \text{ HCHO/ml}$$

Sample Preparation

1. Cut the fabric or paper into small pieces and use the pieces as the test sample.
2. Weigh to the nearest 0.1 mg, 2.5 g of the sample into a 200 ml glass stoppered flask. Add exactly 100 ml deionized water.
3. Stopper securely, and heat the flask in a 40° C. water bath for one hour with occasional shaking.
4. Filter the warm extract through a glass fiber filter and use the filtrate as the test solution.
5. For each sample, identify two 15 ml glass stoppered centrifuge tubes and pipet 5.0 ml of test solution into each tube. Add 5.0 ml acetylacetone solution to one tube and 5.0 ml deionized water to the other tube as a sample blank. Mix well.

Calibration Standards

Identify six glass stoppered centrifuge tubes and transfer the following solutions to each and mix well:

| Tube # | Standard HCHO Solution C (ml) | Deionized Water (ml) | Acetylacetone Solution (ml) |
|---|---|---|---|
| 1 | 0 | 5.0 | 5.0 |
| 2 | 1.0 | 4.0 | 5.0 |
| 3 | 2.0 | 3.0 | 5.0 |
| 4 | 3.0 | 2.0 | 5.0 |
| 5 | 4.0 | 1.0 | 5.0 |
| 6 | 5.0 | 0 | 5.0 |

Heat all tubes in a 40° C. water bath for 30 minutes. Remove the tubes from the bath and allow them to cool for 30 minutes. Zero the spectrophotometer with deionized water and determine the absorbence of the solutions at 412 nm. Prepare a calibration curve. Plot the absorbence of the six calibration standards against the quantity of formaldehyde.

Based on a reading of the ug of formaldehyde from the calibration curve, the concentration of formaldehyde in ppm can be calculated as follows:

$$\text{ppm HCHO} = \frac{\mu g \text{ HCHO (from curve)}}{5.0 \text{ ml}} \times \frac{100 \text{ ml}}{\text{Sample Weight (g)}}$$

The relative precision of the method is ±4.9% at formaldehyde levels of 26 ppm.

TABLE II

| | | | | FORMALDEHYDE CONTENT (PPM) | |
|---|---|---|---|---|---|
| | | | | CHROMATOGRAPHY PAPER ADD-ON LEVEL | |
| RUN | % NMA | % AM | EMULSION | 10% | 20% |
| 1 | 2.4 | 1.99 | 188 | 3.16 | 1.57 |
| 2 | 1.75 | 1.23 | — | 4.65 | 10.26 |
| 3 | 2.5 | 2.5 | 405 | 1.57 | 3.88 |
| 4 | 1.75 | 2.0 | 329 | 3.29 | 6.73 |
| 5 | 2.0 | 2.0 | 404 | 4.40 | 8.83 |
| 6 | 3.5 | 3.0 | 567 | 11.00 | 16.1 |
| 7 | 1.75 | 1.5 | 377 | 6.12 | 6.14 |
| 8 | 3.5 | — | 732 | 13.03 | 31.0 |
| STD | 5 | — | — | — | 96.5 |
| PAPER BLANK #1 | | | | 8.67 | |
| PAPER BLANK #2 | | | | 4.26 | |

Table II shows that the binder emulsions of Runs 1–5 and 7 yielded webbed formaldehyde concentrations comparable to the chromatography paper blanks. Moreover, there does not appear to be a relationship between the free formaldehyde content of the N-methylol acrylamide-acrylamide binder emulsion and of the resulting coated paper web. For example, Runs 1 and 3 which had free formaldehyde concentrations of 188 and 405, respectively, in the binder emulsion afforded cured products having a comparable free formaldehyde content. Accordingly, it appears to be irrelevant to the residual free formaldehyde content of the nonwoven product whether the N-methylol acrylamide-acrylamide binder emulsion is prepared from a monomer solution which is relatively high or low in its level of free formaldehyde.

In addition, Runs 1 and 3, which contained about 50% of the N-methylol acrylamide that was present in the standard emulsion run (STD) plus an amount of acrylamide, yielded cured padded paper samples at 20% add-on having free formaldehyde levels more than 50% below that of the cured papers padded with the standard.

A similar result is also seen comparing Runs 2, 4 and 7 with Run 8. Runs 2, 4 and 7 contained 1.75% N-methylol acrylamide, which was one-half of the 3.5% N-methylol acrylamide content in Run 8. However, the presence of various amounts of acrylamide in Runs 2, 4 and 7 resulted in the free formaldehyde content of the padded papers being less than one-half that for paper padded with the emulsion of Run 8.

It can be seen from Table II that a nonwoven product having low free formaldehyde can be prepared from a binder emulsion comprising an interpolymer of vinyl acetate/ethylene/N-methylol acrylamide/acrylamide which contains about 5–40 wt % ethylene and a mixture of N-methylol acrylamide and acrylamide which is about 3.0 to 10 wt % of the interpolymer, preferably about 4 to about 5 wt %, with the N-methylol acrylamide at about 1.75 to 3.5 wt % and the acrylamide at about 1.25 to 8.25 wt %. When the total of N-methylol acrylamide and acrylamide is about 4 to 5 wt %, the acrylamide will be about 1.25 to 3.25 wt %.

EXAMPLE III

The binder emulsions of Runs 1 and 3 were evaluated at higher add-ons with polyester and were compared to a standard binder emulsion (STD) which was an Airflex-105 emulsion marketed by Air Products & Chemicals, Inc. of Allentown, PA and comprised a vinyl acetate/ethylene/N-methylol acrylamide interpolymer containing 5 wt % N-methylol acrylamide based on the interpolymer. Each binder emulsion, diluted to about 9.0% solids and containing 1% ammonium chloride based on polymer solids, was padded onto a developmental rando polyester web (lightly bonded) supplied by I.P. (Formed Fabrics Division). The padded web was dried 5 minutes at about 300° F. (149° C.) then conditioned overnight in a controlled temperature and humidity room for pick-up determination. The webs were tested for free formaldehyde.

TABLE III

| RUN | % BINDER ADD-ON | FORMALDEHYDE CONTENT OF POLYESTER (PPM) |
|---|---|---|
| 1 | 48 | 6.3 |
| 3 | 51 | 12.6 |
| STD | 50 | 77.7 |
| Polyester Blank | — | 2.5 |

The data in Table III shows that the binder emulsions of Runs 1 and 3 contributed about 4 ppm and 10 ppm formaldehyde respectively. The standard binder emulsion (STD) containing only N-methylol acrylamide (5 wt % based on interpolymer) contributed about 75 ppm free formaldehyde to the polyester web. Once again Runs 1 and 3, which contained about 2.5 wt % N-methylol acrylamide and an amount of acrylamide, yielded a cured product having a free formaldehyde content less than 50% that of the standard emulsion.

EXAMPLE IV

In this example the wet and dry tensile strengths of a chromatography paper padded to a 20% binder add-on using a binder emulsion in accordance with the invention were compared to that of a standard N-methylol acrylamide containing binder emulsion (STD) which was the Airflex-105 emulsion.

Whatman No. 4 chromatography paper was padded with the aqueous emulsion containing 1% ammonium chloride as a curing catalyst. The padded paper was heated 5 minutes at 300° F. (149° C.) and then conditioned overnight in a controlled temperature and humidity room. Some of the padded paper was heated for an additional 3 minutes at 300° F. (149° C.). These reheated samples were also conditioned overnight in the controlled temperature and humidity room. All the samples were tested for tensile strengths according to the testing procedure TAPPI Useful Method #656.

Table IV provides data with respect to the neat emulsions and the padding formulations as well as the data with respect to wet and dry tensile strengths. It can be seen that the greater percent increase in tensile strength with extra heating which is exhibited by the emulsion of Run 1 indicates that it is curing more slowly initially than the standard binder emulsion.

TABLE IV

| SAMPLE | NEAT EMULSION | | | PADDING FORMULATION | | | % BINDER ADD-ON | CMD TENSILE STRENGTH (lb./in.) | | | | | |
|---|---|---|---|---|---|---|---|---|---|---|---|---|---|
| | | | BROOK. VISC. 60 ppm, cps | | | | | 5 min./300° F. CURE | | | ADDITIONAL 3 min./300° F. CURE | | |
| | % CENCO SOLIDS | pH | | % CENCO SOLIDS | pH | CATALYST | | DRY | WET[a] | PERCHLORO | DRY | WET[a] | PERCHLORO |
| RUN 1 | 54.1 | 4.7 | 220 | 8.7 | 5.5 | 1% NH₄Cl | 21 | 13.4 | 6.5 | 6.2 | 16.1 | 9.0 | 8.6 |
| STANDARD | 52.0 | 5.5 | 880 | 8.5 | 6.6 | 1% NH₄Cl | 23 | 16.2 | 9.3 | 8.6 | 18.4 | 10.8 | 9.8 |

[a]Saturated in 1% Aerosol OT aqueous solution for 3 min.

STATEMENT OF INDUSTRIAL APPLICATION

The invention provides a nonwoven product bonded together with a binder comprising an interpolymer of vinyl acetate/ethylene/N-methylol acrylamide/acrylamide. Such nonwoven products which are characterized as having low residual free formaldehyde and good tensile strength are especially suited for making disposable diapers and other paper nonwovens.

I claim:

1. A nonwoven product comprising a nonwoven web of fibers bonded together with a binder which comprises an interpolymer of vinyl acetate/ethylene/an N-methylol acrylamide/an acrylamide, the interpolymer containing about 5 to 40 wt % ethylene and an amount of the N-methylol acrylamide and the acrylamide which is about 3 to 10 wt % of the interpolymer, the N-methylol acrylamide being about 1.75 to 3.5 wt % and the acrylamide about 1.25 to 8.25 wt %, the nonwoven product characterized by a low free formaldehyde content after drying and curing at a binder add-on which is sufficient to bind the fibers together to form a self-sustaining web.

2. The nonwoven product of claim 1 in which the free formaldehyde content after drying and curing is less than about 50 ppm.

3. The nonwoven product of claim 2 having at least about 3 wt% binder add-on, on a dry basis.

4. The nonwoven product of claim 3 having about 50 wt% binder add-on, on a dry basis.

5. The nonwoven product of claim 1 in which the free formaldehyde content is less than 25 ppm.

6. The nonwoven product of claim 3 in which the free formaldehyde content is less than 25 ppm.

7. The nonwoven product of claim 6 having about a 50 wt% binder add-on, on a dry basis.

8. The nonwoven product of claim 3 in which the interpolymer is vinyl acetate/ethylene/N-methylol acrylamide/acrylamide.

9. The nonwoven product of claim 8 in which the interpolymer contains an amount of N-methylol acrylamide and acrylamide which is about 4 to 5 wt% of the interpolymer, the acrylamide being about 1.25 to 3.25 wt%.

10. The nonwoven product of claim 8 in which the interpolymer contains N-methylol acrylamide and acrylamide in about equal molar amounts.

11. The nonwoven product of claim 1 which is a paper nonwoven product.

12. The nonwoven product of claim 1 in which the fibrous web comprises synthetic polymeric fibers.

13. The nonwoven product of claim 1 in which the fibrous web comprises natural polymeric fibers.

14. The nonwoven product of claim 11 having a free formaldehyde content of less than about 10 ppm at about 20 wt% or less binder add-on, on a dry basis.

15. The nonwoven product of claim 8 which is a paper nonwoven.

16. The nonwoven product of claim 8 in which the fibrous web comprises synthetic polymeric fibers.

17. The nonwoven product of claim 8 in which the fibrous web comprises natural polymeric fibers.

18. The nonwoven product of claim 15 having a free formaldehyde content of less than about 10 ppm at about 20 wt% or less binder add-on, on a dry basis.

19. A nonwoven product formed from a nonwoven web of fibers bonded together by a binder deposited from an interpolymer latex comprising an aqueous medium having dispersed threrein a vinyl acetate/ethylene/an N-methylol acrylamide/an acrylamide interpolymer, the interpolymer containing about 5 to 40 wt% ethylene and an amount of the N-methylol acrylamide and the acrylamide which is about 3 to 10 wt% of the interpolymer, the N-methylol acrylamide being about 1.75 to 3.5 wt% and the acrylamide about 1.25 to 8.25 wt%, the nonwoven product characterized by a free formaldehyde content after drying and curing of less than 50 ppm at a binder add-on which is sufficient to bind the fibers together to form a self-sustaining web.

20. The nonwoven product of claim 19 having at least about 3 wt% binder add-on, on a dry basis.

21. The nonwoven product of claim 20 having a free formaldehyde content of less than 25 ppm.

22. A nonwoven product of claim 21 having about a 50 wt% binder add-on, on a dry basis.

23. The nonwoven product of claim 21 in which the binder is a vinyl acetate/ethylene/N-methylol acrylamide/acrylamide interpolymer.

24. The nonwoven product of claim 23 in which the interpolymer contains an amount of N-methylol acrylamide and acrylamide which is about 4 to 5 wt% of the interpolymer, the acrylamide being about 1.25 to 3.25 wt%.

25. The nonwoven product of claim 23 in which the interpolymer contains N-methylol acrylamide and acrylamide in about equal molar amounts.

26. The nonwoven product of claim 19 having a free formaldehyde content of less than 10 ppm.

27. A nonwoven fabric having a low residual free formaldehyde content comprising a loosely assembled web of fibers bonded together with a binder which comprises an interpolymer of vinyl acetate/ethylene/N-methylol acrylamide/acrylamide, the interpolymer containing about 5 to 40 wt% ethylene and an amount of N-methylol acrylamide and acrylamide which is about 3.0 to 10 wt% of the interpolymer, the N-methylol acrylamide being about 1.75 to 3.5 wt% and the acrylamide about 1.25 to 8.25 wt%, the nonwoven fabric characterized by a free formaldehyde content after drying and curing of less than 50 to 60 ppm at a 10 to 100 wt% binder add-on, on a dry basis.

28. The invention of claim 27 in which the interpolymer contains an amount of N-methylol acrylamide and acrylamide which is about 4 to 5 wt% of the interpolymer, the acrylamide being about 1.25 to 3.25 wt%.

29. The invention of claim 27 in which the interpolymer contains N-methylol acrylamide and acrylamide in about equal molar amounts.

30. The invention of claim 27 in which the nonwoven fabric is a disposable diaper.

31. The invention of claim 27 in which the nonwoven fabric is characterized by a residual free formaldehyde content of less than 30 ppm at a 20 wt% binder add-on, on a dry basis.

32. A nonwoven fabric having a low residual free formaldehyde content formed from a loosely assembled web of fibers bonded together by a binder deposited from a vinyl acetate/ethylene/N-methylol acrylamide/acrylamide interpolymer latex comprising an aqueous medium having colloidally suspended therein a vinyl acetate/ethylene/N-methylol acrylamide/acrylamide interpolymer, the interpolymer containing about 5 to 40 wt% ethylene and an amount of N-methylol acrylamide and acrylamide which is about 3.0 to 10 wt% of the interpolymer, the N-methylol acrylamide being about 1.75 to 3.5 wt% and the acrylamide about 1.25 to 8.25 wt%, the nonwoven fabric characterized by a free formaldehyde content after drying and curing of less than 50 to 60 ppm at a 10 to 100 weight % binder add-on, on a dry basis.

33. The invention of claim 32 in which the interpolymer contains an amount of N-methylol acrylamide and acrylamide which is about 4 to 5 wt% of the interpolymer, the acrylamide being about 1.25 to 3.25 wt%.

34. The invention of claim 32 in which the interpolymer contains N-methylol acrylamide and acrylamide in about equal molar amounts.

35. The invention of claim 32 in which the nonwoven fabric is a disposable diaper.

36. The invention of claim 32 in which the nonwoven fabric is characterized by a residual free formaldehyde content of less than 30 ppm at a 20% binder add-on, on a dry basis.

37. A method for the preparation of a nonwoven product which comprises applying to a nonwoven mass of fibers a latex comprising an interpolymer of vinyl acetate/ethylene/an N-methylol acrylamide/an acrylamide dispersed in water, the interpolymer containing about 5 to 40 wt% ethylene and an amount of the N-methylol acrylamide and acrylamide which is about 3 to 10 wt% of the interpolymer, the N-methylol acrylamide being about 1.75 to 3.5 wt% and the acrylamide about 1.25 to 8.25 wt%, heating to remove the water and to bond the fibers together with the interpolymer, the latex being applied to the nonwoven mass of fibers to provide a sufficient amount of interpolymer add-on to bind the fibers together to form a self-sustaining web, and the nonwoven product characterized by a low free formaldehyde content.

38. The method of claim 37 in which the nonwoven product has a free formaldehyde content of less than 50 ppm.

39. The method of claim 38 in which the latex is applied to the mass of fibers in an amount to provide at least about 3 wt% interpolymer add-on, on a dry basis.

40. The method of claim 39 in which the nonwoven product has a free formaldehyde content of less than 25 ppm.

41. The method of claim 39 in which the latex comprises an interpolymer of vinyl acetate/ethylene/N-methylol acrylamide/acrylamide dispersed in water.

42. A method for the preparation of a nonwoven fabric having a low residual free formaldehyde content which comprises applying to a loosely assembled mass of fibers a latex comprising an interpolymer of vinyl acetate/ethylene/N-methylol acrylamide/acrylamide colloidally suspended in water, the interpolymer containing about 5 to 40 wt% ethylene and an amount of N-methylol acrylamide and acrylamide which is about 3.0 to 10 wt% of the interpolymer, the N-methylol acrylamide being about 1.75 to 3.5 wt% and the acrylamide about 1.25 to 8.25 wt%, heating to remove the water and to bond the fibers together with the interpolymer, the latex being applied to the mass of fibers in an amount to provide a 10 to 100 weight % interpolymer add-on, on a dry basis, and the nonwoven fabric characterized by a free formaldehyde content of less than 50 to 60 ppm.

43. The invention of claim 42 in which the interpolymer contains an amount of N-methylol acrylamide and acrylamide which is about 4 to 5 wt% of the interpolymer, the acrylamide being about 1.25 to 3.25 wt%.

44. The invention of claim 42 in which the interpolymer contains N-methylol acrylamide and acrylamide in about equal molar amounts.

45. The invention of claim 42 in which the nonwoven fabric is a disposable diaper.

46. The invention of claim 42 in which the nonwoven fabric is characterized by a residual free formaldehyde content of less than 30 ppm at a 20 wt% binder add-on, on a dry basis.

* * * * *